(12) United States Patent
Mallard

(10) Patent No.: US 10,744,112 B2
(45) Date of Patent: Aug. 18, 2020

(54) COMPOSITION COMPRISING AVERMECTIN COMPOUNDS WITHOUT SOLVENTS AND PROPENETRATING AGENTS OF AVERMECTIN COMPOUNDS

(71) Applicant: Nestlé Skin Health SA, Lausanne (CH)

(72) Inventor: Claire Mallard, Mougins (FR)

(73) Assignee: NESTLÉ SKIN HEALTH S.A., Lausanne (CH)

( * ) Notice: Subject to any disclaimer, the term of this patent is extended or adjusted under 35 U.S.C. 154(b) by 0 days.

(21) Appl. No.: 16/463,814

(22) PCT Filed: Nov. 23, 2017

(86) PCT No.: PCT/EP2017/080148
§ 371 (c)(1),
(2) Date: May 23, 2019

(87) PCT Pub. No.: WO2018/096010
PCT Pub. Date: May 31, 2018

(65) Prior Publication Data
US 2019/0274995 A1  Sep. 12, 2019

(30) Foreign Application Priority Data
Nov. 24, 2016 (EP) .................................. 16306554

(51) Int. Cl.
| | | |
|---|---|---|
| *A61K 9/00* | (2006.01) | |
| *A61K 31/343* | (2006.01) | |
| *A61P 17/00* | (2006.01) | |
| *A61K 9/10* | (2006.01) | |
| *A61K 31/7048* | (2006.01) | |
| *A61K 9/06* | (2006.01) | |
| *A61P 17/10* | (2006.01) | |
| *A61K 9/107* | (2006.01) | |

(52) U.S. Cl.
CPC .......... *A61K 31/343* (2013.01); *A61K 9/0014* (2013.01); *A61K 9/06* (2013.01); *A61K 9/10* (2013.01); *A61K 9/107* (2013.01); *A61K 31/7048* (2013.01); *A61P 17/00* (2018.01); *A61P 17/10* (2018.01)

(58) Field of Classification Search
None
See application file for complete search history.

(56) References Cited

U.S. PATENT DOCUMENTS

| | | | |
|---|---|---|---|
| 5,773,422 A | 6/1998 | Komer | |
| 8,858,967 B2 * | 10/2014 | Astruc | A61K 9/0014 424/401 |
| 2005/0143325 A1 | 6/2005 | Guzzo et al. | |
| 2006/0100165 A1 | 5/2006 | Manetta et al. | |
| 2007/0116731 A1 | 5/2007 | Astruc et al. | |
| 2008/0214657 A1 | 9/2008 | Spring et al. | |
| 2009/0035338 A1 | 2/2009 | Segura-Orsoni et al. | |
| 2009/0233877 A1 | 9/2009 | Kaoukhov et al. | |
| 2009/0264378 A1 | 10/2009 | Kaoukhov et al. | |
| 2010/0093652 A1 | 4/2010 | Spring et al. | |
| 2012/0004200 A1 | 1/2012 | Nadau-Fourcade et al. | |
| 2013/0108563 A1 | 5/2013 | Diaz-Astruc et al. | |
| 2015/0105340 A1 | 4/2015 | Spring et al. | |
| 2016/0303152 A1 * | 10/2016 | Nayar ................ A61K 31/7048 | |
| 2016/0303154 A1 | 10/2016 | Nayar | |
| 2016/0303155 A1 | 10/2016 | Nayar | |

FOREIGN PATENT DOCUMENTS

| | | |
|---|---|---|
| CN | 101773470 | 7/2010 |
| FR | 2 924 944 A1 | 6/2009 |
| WO | WO-2016/022066 A1 | 2/2016 |
| WO | WO-2016/024855 A1 | 2/2016 |
| WO | WO-2016024855 A1 * | 2/2016 ......... A61K 31/7048 |

OTHER PUBLICATIONS

International Search Report issued in PCT/EP2017/080146 and dated Jan. 30, 2018.
International Search Report issued in PCT/EP2017/080147 and dated Jan. 24, 2018.
International Search Report issued in PCT/EP2017/080148 and dated Feb. 6, 2018.
Communication pursuant to Article 94(3) EPC dated Mar. 23, 2020 issued in corresponding European Application No. 16306554.3 (4 pages).

* cited by examiner

*Primary Examiner* — Robert A Wax
*Assistant Examiner* — Melissa S Mercier
(74) *Attorney, Agent, or Firm* — Foley & Lardner LLP; S. Talapatra

(57) ABSTRACT

Composition comprising avermectin compounds without solvents and propenetrating agents of avermectin compounds The invention relates to a dermatological or pharmaceutical composition comprising at least one aqueous phase and at least one fatty phase comprising one or more fatty compounds different from solvents and/or propenetrating agents of avermectin compounds and a least one active compound chosen from avermectin compounds, where the composition comprises neither solvents nor propenetrating agents of avermectin compounds. The invention relates also to the composition for use in the treatment of rosacea, of common acne, of seborrheic dermatitis, of perioral dermatitis, of acneiform rashes, of transient acantholytic dermatosis, of acne necrotica miliaris and of atopic dermatitis, and preferably for use in the treatment of rosacea. Finally, the invention relates to a method for preparing the composition.

15 Claims, No Drawings

COMPOSITION COMPRISING AVERMECTIN COMPOUNDS WITHOUT SOLVENTS AND PROPENETRATING AGENTS OF AVERMECTIN COMPOUNDS

CROSS-REFERENCE TO RELATED APPLICATIONS

This application is a National Phase of International Patent Application No. PCT/EP2017/080148, filed Nov. 23, 2017, published on May 31, 2018 as WO 2018/096010 A1, which claims priority to European Patent Application No. 16306554.3, filed Nov. 24, 2016. The contents of these applications are herein incorporated by reference in their entirety.

The invention relates to a dermatological or pharmaceutical composition comprising at least one active compound chosen from avermectin compounds without solvents and propenetrating agents of avermectin compounds.

In particular, the invention relates to a dermatological or pharmaceutical composition comprising at least one aqueous phase and at least one fatty phase comprising one or more fatty compounds different from solvents and/or propenetrating agents of avermectin compounds and at least one active compound chosen from avermectin compounds, where the composition comprises neither solvents nor propenetrating agents of avermectin compounds.

The invention relates also to the composition for use in the treatment of rosacea, of common acne, of seborrheic dermatitis, of perioral dermatitis, of acneiform rashes, of transient acantholytic dermatosis, of acne necrotica miliaris and of atopic dermatitis, and preferably for use in the treatment of rosacea.

Finally, the invention relates to a method for preparing the composition.

The class of avermectins, a group of macrocyclic lactones produced by the bacterium *Streptomyces avermitilis* (Reynolds JEF (Ed) (1993) Martindale, The extra pharmacopoeia, 29$^{th}$ Edition, Pharmaceutical Press, London), namely includes ivermectin, invermectin, avermectin, abamectin, doramectin, eprinomectin, and selamectin.

In particular, ivermectin is a mixture of two compounds, 5-O-demethyl-22,23-dihydroavermectin $A_{1a}$ and 5-O-demethyl-22-23-dihydroavermectin $A_{1b}$.

In the middle of the 1980s, ivermectin was presented as a broad-spectrum anti-parasitic medicinal product for veterinary use (W. C. CAMPBELL, et al., (1983) "Ivermectin: a potent new anti-parasitic agent", Science, 221, 823-828). It is effective against most common intestinal worms (except tapeworms), most acarids and some lice. It in particular exhibits considerable affinity for the glutamate-dependent chloride channels present in invertebrate nerve cells and muscle cells. Its binding to these channels promotes an increase in membrane permeability to chloride ions, resulting in hyperpolarization of the nerve or muscle cell. Neuromuscular paralysis which can lead to the death of certain parasites results therefrom. Ivermectin also interacts with other ligand-dependent chloride channels, such as those involving the neuromediator GABA (gamma-aminobutyric acid).

Ivermectin is more particularly an anthelmintic. It has been administered in humans in the treatment of onchocerciasis caused by *Onchocerca volvulus*, of gastrointestinal strongyloidias (anguillulosis) and of human scabies and also in the treatment of microfilaremia diagnosed or suspected in individuals suffering from lymphatic filariosis due to *Wuchereria bancrofti*.

More recently, compounds of avermectin family have been used in the treatment of dermatological conditions such as rosacea in a topical pharmaceutical composition suited for human administration.

Dermatological conditions are often associated with increased sensitivity of the skin, particularly in the case of rosacea which is an inflammatory dermatosis that affects mainly the central part of the face and is characterized, inter alia, by reddening of the face, hot flashes and facial erythema.

This type of pathology requires in particular the application of pharmaceutical formulations that are easy to spread and give the user a pleasant feeling of well-being.

For example, the document US 2006/0100165 describes the use of topical compositions comprising ivermectin for the treatment of dermatological conditions such as rosacea. In order to obtain compositions which are physically and chemically stable over time, ivermectin is formulated with propenetrating agents and/or solvents, especially propylene glycol, oleyl alcohol and phenoxyethanol.

However, these solvents and/or propenetrating agents could be irritating for sensitive skin, namely skin afflicted by rosacea.

There is therefore a need to manufacture compositions comprising avermectin compounds, especially ivermectin, which are less irritating for sensitive skin, in particular skin afflicted by rosacea, without impeding on the chemical and physical stability over time of these compositions.

In addition, there is a need to simplify compositions based on avermectin compounds by reducing the number of ingredients which is in favour of having a better tolerated formulation for sensitive skin.

It has now been found, surprisingly, that a dermatological or pharmaceutical composition comprising at least one active compound chosen from avermectin compounds without solvents and propenetrating agents of avermectin compounds, presents a better tolerance for the sensitive skin and in particular can reduce irritation disorders on sensitive skin such as rosacea skin while having good chemical and physical stability over time.

The present invention thus concerns a dermatological or pharmaceutical composition comprising at least one aqueous phase and at least one fatty phase comprising one or more fatty compounds different from solvents and/or propenetrating agents of avermectin compounds and at least one active compound chosen from avermectin compounds, where the composition comprises neither solvents nor propenetrating agents of avermectin compounds.

The composition according to the invention presents a better tolerance for the sensitive skin and therefore can be used on sensitive skin i.e. skin affected by dermatological afflictions/conditions such as rosacea skin.

In addition, the composition according to the invention exhibits good chemical and physical stability over time, even at a temperature above ambient temperature (for example, 40° C.).

"Chemical stability" means that the amount of avermectin compounds of the composition does not change more than 5% by weight relative to the initial amount of avermectin compounds of the composition during 1 month, preferably during 2 months and even more preferably during 3 months.

"Physical stability" means that the composition meets the acceptance criteria for appearance, physical attributes and functionality test (e.g. color, phase separation, dose delivery per actuation). More precisely the physical stability means that at least two of the following criteria, preferably all of the following criteria: microscopic aspect, macroscopic aspect, viscosity and pH, do not significantly vary after manufacture time during 1 months, preferably during 2 months and even more preferably during 3 months.

The present invention also concerns the dermatological or pharmaceutical composition as defined above for use in the treatment of rosacea, of common acne, of seborrheic dermatitis, of perioral dermatitis, of acneiform rashes, of transient acantholytic dermatosis, of acne necrotica miliaris and of atopic dermatitis, and preferably for use in the treatment of rosacea.

The invention concerns also a method for preparing the composition comprising the following steps:

a) mixing avermectin compounds with at least one fatty compound, until the avermectin compounds are solubilized, in order to form the fatty phase;

b) mixing the constituents of the aqueous phase to homogeneity;

c) incorporating the fatty phase into the aqueous phase so as to form the composition.

In particular, during the preparation of the composition of the present invention, it has been observed that the avermectin compounds have been solubilized in the fatty phase despite of the fact that the said fatty phase does not comprise (or is devoided of) solvents and propenetrating agents.

Hence, the avermectin compounds are solubilized into the final composition thanks to their solubilization into the fatty phase.

Other subject-matters, characteristics, aspects and advantages of the invention will become even more clearly apparent on reading the description and the examples which follow.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more".

As described above, the composition according to the invention comprises neither solvents nor propenetrating agents of avermectin compounds.

A solvent of avermectin compounds is defined as a liquid compound in which the compounds of the avermectin family, in particular ivermectin, have a solubility at room temperature and at atmospheric pressure of more than or equal to 2% by weight relative to the composition comprising only said solvent or said solvent in association with one or more solvents of avermectin compounds.

Solubility of a compound into one or more solvents is defined as the amount of compound that passes into a solution constituted of the one or more solvents to achieve a saturated solution at constant temperature and pressure (stirring of the saturated solution from 16 to 24 hours). Solubility is expressed in terms of maximum volume or mass of the compound that dissolves in a given volume or mass of one or more solvents.

A propenetrating agent of avermectin compounds makes it possible to facilitate the penetration of the compounds of the avermectin family into the skin, preferably dissolves said compounds present in the composition according to the invention.

Preferably, solvents and propenetrating agents of avermectin compounds are chosen from propylene glycol, ethanol, isopropanol, butanol, N-methyl-2-pyrrolidone, dimethylsulfoxyde, polysorbate 80, poloxamer 124, phenoxyethanol, oleyl alcohol, isostearic acid, diisopropyl adipate, polypropylene glycol-15 stearyl ether ("PPG-15 stearyl ether"), octyl dodecanol, ethyl oleate, $C_{12}$-$C_{15}$ alkyl benzoate and mixtures thereof.

Thus, the dermatological or pharmaceutical composition according to the invention preferably comprises none of these compounds, that is to say the dermatological or pharmaceutical composition according to the invention preferably does not comprise propylene glycol, ethanol, isopropanol, butanol, N-methyl-2-pyrrolidone, dimethylsulfoxyde, polysorbate-80, poloxamer 124, phenoxyethanol, oleyl alcohol, isostearic acid, diisopropyl adipate, PPG-15 stearyl ether, octyl dodecanol, ethyl oleate, $C_{12}$-$C_{15}$ alkyl benzoate.

The avermectin compounds that are used according to the invention are preferably selected from ivermectin, invermectin, avermectin, abamectin, doramectin, eprinomectin and selamectin.

Preferably, the avermectin compound is ivermectin.

The composition according to the invention comprises preferably from 0.01 to 10% by weight, more preferably from 0.1 to 5% by weight of avermectin compounds, relative to the total weight of the composition.

The composition according to the invention comprises one or more fatty compounds in the fatty phase different from solvents and/or propenetrating agents of avermectin compounds which are preferably chosen from vegetable, mineral, animal or synthetic oils, silicone oils, fatty acids, fatty alcohols, waxes, gums, and mixtures thereof.

As an example of a mineral oil, mention may be made, for example, of paraffin oils of various viscosities, such as Primol 352, Marcol 82 or Marcol 152 marketed by Univar.

As a vegetable oil, mention may be made of sweet almond oil, palm oil, soybean oil, sesame oil and sunflower oil.

As an animal oil, mention may be made of lanolin, squalene, fish oil and mink oil.

As a synthetic oil, mention may be made of fatty acid alcohol esters, such as cetearyl isononanoate marketed in particular under the name Cetiol SN by BASF, isopropyl palmitate, for instance the product marketed under the name Crodamol IPP by Croda, or caprylic capric triglyceride such as Miglyol 812 marketed by IMCD.

As a silicone oil, mention may be made of a dimethicone, such as the product marketed under the name Dow Corning 200 fluid, or a cyclomethicone, such as the product marketed under the name Dow Corning 244 fluid by Dow Corning, or the product marketed under the name Mirasil CMS by Bluestar Silicones.

As fatty acid, mention may be made of stearic acid.

As a fatty alcohol, mention may be made of stearyl alcohol, cetostearyl alcohol and cetyl alcohol.

As wax, mention may be made of beeswax, carnauba wax and candelilla wax.

As gum, mention may be made of silicone gums.

More preferably, said fatty compounds are chosen from fatty acid alcohol esters, silicone oils, fatty alcohols, and mixtures thereof.

The dermatological or pharmaceutical composition according to the invention may comprise from 5 to 30% by weight, preferably from 10 to 20% by weight of fatty compounds, relative to the total weight of the composition.

The composition according to the invention may comprise one or more surfactants.

Preferably, the surfactants are chosen from non-ionic surfactants.

More preferably the surfactants are chosen from polyoxyethylenated fatty alcohol ethers, sorbitan esters, and mixtures thereof.

As a polyoxyethylenated fatty alcohol ether, mention may be made of ceteareth-20.

As a sorbitan ester, mention may be made of sorbitan monostearate.

The dermatological or pharmaceutical composition according to the invention may comprise from 0.1 to 10% by weight, preferably from 1 to 7% by weight of surfactants, relative to the total weight of the composition.

The composition according to the invention may optionally comprise at least one gelling agent, preferably at least one aqueous phase gelling agent.

Among the gelling agents which can be used in the composition according to the invention, mention may be made of carboxyvinyl polymers (carbomers) and, by way of non-limiting examples, of carbomer, Carbopol 981, Carbopol ETD 2020, Carbopol 980, Carbopol Ultrez 10 NF and Pemulen TR1, marketed by Lubrizol.

Preferably, the gelling agents are chosen from acrylates/$C_{10-30}$ alkyl acrylate crosspolymer (Pemulen TR1).

As gelling agent according to the invention, use will preferably be made of carbomers, and preferably Pemulen TR1.

The composition of the invention preferentially contains from 0.01 to 5%, and preferably from 0.1 to 3%, of gelling agents.

Preferably, the gelling agents are in the aqueous phase of the composition.

In a particular embodiment of the invention, the composition comprises one or more antioxidant agents.

As antioxidant agent, mention may be made of butylhydroxyanisole, tocopherol, tocopherol acetate, ascorbic acid, ascorbic palmitate, propyl gallate, sodium metabisulfite, butylhydroxytoluene, and mixture thereof.

More preferably in this particular embodiment, the composition comprises butylhydroxytoluene.

Thus it has been found that the use of butylhydroxytoluene into the composition is particularly interesting as it allows to improve even more the physical and chemical stability of the composition.

In said particular embodiment, the composition comprises preferably from 0.001 to 2% by weight, more preferably from 0.01 to 1% by weight of antioxidant agents, relative to the total weight of the composition.

Preferably, the antioxidant agents are in the fatty phase of the composition.

The aqueous phase of the composition according to the invention comprises water.

The composition according to the invention may also contain inert additives or combinations of these additives, such as flavor enhancers; preservatives; stabilizers; humidity regulators; pH regulators; osmotic pressure modifiers; and UV-A and UV-B screening agents.

Of course, one skilled in this art will take care to choose the optional compound(s) to be added to the composition of the invention in such a way that the advantageous properties intrinsically associated with the present invention are not, or are not substantially, altered by the envisaged addition.

These additives may be present in the composition at from 0.001 to 20% by weight relative to the total weight of the composition.

As described above, the composition according to the invention comprises at least one fatty phase and at least one aqueous phase.

Preferably, the composition according to the invention is suited for treating the skin and can be in liquid, pasty or solid form, and more particularly in the form of ointments, creams, milks, pomades, powders, impregnated pads, syndets, towelettes, solutions, gels, sprays, foams, suspensions, lotions, sticks, shampoos or washing bases.

It may also be in the form of suspensions of microspheres or nanospheres or of lipid or polymeric vesicles or of polymeric patches and of hydrogels for controlled release.

More preferably, the composition according to the invention is in liquid form.

Preferably, the composition according to the invention is in the form of an oil-in-water emulsion, i.e., the fatty phase being dispersed in the aqueous phase.

More preferably, the composition according to the invention is in the form of an oil-in-water liquid emulsion.

The composition according to the invention comprises preferably from 10 to 90% of fatty phase and from 10 to 90% of aqueous phase, more preferably said composition comprises from 10 to 30% of fatty phase and from 70 to 90% of aqueous phase.

The pH will preferably range from 5.0 to 7.0, more preferably from 6.0 to 6.5.

Verification of the natural pH of the mixture and possible correction with a solution of a neutralizing agent, and also the incorporation of the optional additives, may be carried out, according to their chemical nature, during one of the steps of the method of preparation, described below.

In a particular embodiment, the composition according to the invention comprises:
  at least one fatty phase comprising from 5 to 30% by weight, preferably from 10 to 20% by weight of fatty compounds different from solvents and/or propenetrating agents of avermectin compounds, relative to the total weight of the composition, and from 0.01 to 10% by weight, preferably from 0.1 to 5% by weight of avermectin compounds,
  at least one aqueous phase,
  where the composition comprises neither solvents nor propenetrating agents of avermectin, preferably does not comprise propylene glycol, ethanol, isopropanol, butanol, N-methyl-2-pyrrolidone, dimethylsulfoxyde, polysorbate 80, poloxamer 124, phenoxyethanol, oleyl alcohol, isostearic acid, diisopropyl adipate, PPG-15 stearyl ether, octyl dodecanol, ethyl oleate and $C_{12}$-$C_{15}$ alkyl benzoate.

More preferably in this embodiment, the composition according to the invention comprises:
  at least one fatty phase comprising from 5 to 30% by weight, preferably from 10 to 20% by weight of fatty compounds different from solvents and/or propenetrating agents of avermectin compounds, relative to the total weight of the composition, and from 0.01 to 10% by weight, preferably from 0.1 to 5% by weight of avermectin compounds, relative to the total weight of the composition,
  at least one aqueous phase,
  from 0.001 to 2% by weight, preferably from 0.01 to 1% by weight of antioxidant agents, relative to the total weight of the composition,
  where the composition comprises neither solvents nor propenetrating agents of avermectin, preferably does not comprise propylene glycol, ethanol, isopropanol, butanol, N-methyl-2-pyrrolidone, dimethylsulfoxyde, polysorbate 80, poloxamer 124, phenoxyethanol, oleyl alcohol, isostearic acid, diisopropyl adipate, PPG-15 stearyl ether, octyl dodecanol, ethyl oleate and $C_{12}$-$C_{15}$ alkyl benzoate.

According to these embodiments, avermectin compound is preferably ivermectin.

According to these embodiments, the compositions preferably comprise at least one gelling agent chosen from acrylates/$C_{10-30}$ alkyl acrylate crosspolymer.

The dermatological or pharmaceutical composition according to the invention is preferably a topical composition.

This composition according to the invention is useful to treat dermatological conditions/afflictions.

In particular, the composition according to the invention is useful for the treatment of rosacea, of common acne, of seborrheic dermatitis, of perioral dermatitis, of acneiform rashes, of transient acantholytic dermatosis, of acne necrotica miliaris and of atopic dermatitis.

More particularly, the dermatological or pharmaceutical composition is used in the treatment of rosacea.

In a particular embodiment, the composition according to the invention is useful in a method for the treatment of rosacea characterized in that the composition is administered topically.

The present invention also features a method for preparing the composition which comprises the following steps:

a) mixing ivermectin with at least one fatty compound, until the ivermectin is solubilized, in order to form the fatty phase;

b) mixing the constituents of the aqueous phase to homogeneity;

c) incorporating the fatty phase into the aqueous phase so as to form the composition.

In order to illustrate the present invention and the advantages thereof, the following specific examples of compositions comprising ivermectin and the physical and chemical stability thereof are given, it being understood that same are intended only as illustrative and in nowise limitative. In said examples to follow, all parts and percentages are given by weight, unless otherwise indicated.

EXAMPLE 1

1) Preparation of the Compositions

The compositions 1 to 3 according to the invention are formulated according to the following procedure:

In a first beaker, weigh the carbomer polymer (Pemulen TR1) and the purified water, mix at 700 rpm and heat to 65° C. (±2° C.) then weigh the rest of the ingredients of the aqueous phase and mix all the aqueous phase.

In a second beaker, weigh the fatty phase without sorbitan monostearate, dimethicone and propyl parahydroxybenzoate, heat at 65° C. (±2° C.), then weigh Ivermectin and mix together. Then weigh sorbitan monostearate and butylhydroxytoluene when present into the composition and mix together. Weigh dimethicone and propyl parahydroxybenzoate then mix all the fatty phase.

Where the fatty and aqueous phases are at 65° C. (±2° C.), mix the two phases with Rayneri stirring at 900 rpm until complete homogeneity, and then cool.

Allow the emulsion to cool to 35° C. (±2° C.) then adjust the pH to 6.0 with the sodium hydroxide solution.

|  | Ingredients | 1 | 2 | 3 |
|---|---|---|---|---|
|  |  | % by weight relative to the total weight of the composition | | |
| Fatty phase | Ivermectin | 1 | 1 | 1 |
|  | Isopropyl palmitate | 4 | 4 | 8 |
|  | Cetyl alcohol | 3.5 | 3.5 | 3.5 |
|  | Stearyl alcohol | 2.5 | 2.5 | 2.5 |
|  | Ceteareth-20 | 3 | 3 | 3 |
|  | Sorbitan monostearate | 2 | 2 | 2 |
|  | Dimethicone | 0.5 | 0.5 | 0.5 |
|  | Propyl parahydroxybenzoate | 0.1 | 0.1 | 0.1 |
|  | Butylhydroxytoluene | — | 0.1 | — |
| Aqueous phase | Pemulen TR1 | 0.2 | 0.2 | 0.2 |
|  | Glycerin | — | 4 | 4 |
|  | Methyl parahydroxybenzoate | 0.2 | 0.2 | 0.2 |
|  | Disodium EDTA | 0.05 | 0.05 | 0.05 |
|  | Citric acid | 0.05 | 0.05 | 0.05 |
|  | Purified water | qs 100 | qs 100 | qs 100 |
|  | 10% sodium hydroxide | qs pH | qs pH | qs pH |

2) Physical and Chemical Stability of the Compositions

Physical and Chemical Characteristics of the Compositions According to the Invention at T0 and at Room Temperature

| Composition | 1 | 2 | 3 |
|---|---|---|---|
| Macroscopic aspect | white cream | white cream | white cream |
| Microscopic aspect | liquid crystals from 3 μm to 15 μm | liquid crystals from 3 μm to 10 μm | liquid crystals from 3 μm to 8 μm |
| pH | 6.21 | 6.33 | 6.12 |
| Viscosity (cP) | 43200 | 42987 | 60053 |
| Ivermectin titer (%/label claim) | 96.7 (CV 0.1%) | 96.8 (CV 0.1%) | 96.5 (CV 0.0%) |

CV: coefficient of variation

The viscosity is measured by the use of a Brookfield Viscometer (RV duII+Small sample adaptator Spindle 34 v=6 rpm).

The compositions according to the invention are physically and chemically stable at T0 and at room temperature.

Physical Stability

The table below represents physical stability of the compositions according to the invention at 5° C., room temperature (RT) and 40° C. during three months.

|  | 1 month | | | 2 months | | |
|---|---|---|---|---|---|---|
| Composition 1 | 5° C. | RT | 40° C. | 5° C. | RT | 40° C. |
| Macroscopic aspect | No change relative to T0 | | | No change relative to T0 | | |
| Microscopic aspect | No change relative to T0 | | | No change relative to T0 | | |
| pH | 6.30 | 6.24 | 6.29 | 6.23 | 6.13 | 6.16 |
| Viscosity (cP) | 43947 | 41920 | 37973 | 45440 | 45547 | 40533 |

|  | 1 month | | | 2 months | | |
|---|---|---|---|---|---|---|
| Composition 2 | 5° C. | RT | 40° C. | 5° C. | RT | 40° C. |
| Macroscopic aspect | No change relative to T0 | | | No change relative to T0 | | |
| Microscopic aspect | No change relative to T0 | | | No change relative to T0 | | |

-continued

| | | | | | | |
|---|---|---|---|---|---|---|
| pH | 6.26 | 6.17 | 6.35 | 6.20 | 6.20 | 6.24 |
| Viscosity (cP) | 44373 | 48640 | 55360 | 45760 | 46933 | 50560 |

| | 3 months | | |
|---|---|---|---|
| | 5° C. | RT | 40° C. |
| Macroscopic aspect | No change relative to T0 | | |
| Microscopic aspect | No change relative to T0 | | |
| pH | 6.19 | 6.14 | 6.28 |
| Viscosity (cP) | 51520 | 53333 | 54080 |

| | 1 month | | | 2 months | | |
|---|---|---|---|---|---|---|
| Composition 3 | 5° C. | RT | 40° C. | 5° C. | RT | 40° C. |
| Macroscopic aspect | No change relative to T0 | | | No change relative to T0 | | |
| Microscopic aspect | No change relative to T0 | | | No change relative to T0 | | |
| pH | 6.15 | 6.20 | 6.18 | 6.25 | 6.16 | 6.32 |
| Viscosity (cP) | 54080 | 58880 | 54613 | 54720 | 55573 | 54080 |

| | 3 months | | |
|---|---|---|---|
| | 5° C. | RT | 40° C. |
| Macroscopic aspect | No change relative to T0 | | |
| Microscopic aspect | No change relative to T0 | | |
| pH | 6.16 | 6.12 | 6.20 |
| Viscosity (cP) | 54400 | 55360 | 47893 |

Composition 1 is physically stable two months at 5° C., room temperature and 40° C.

Compositions 2 and 3 are physically stable three months at 5° C., room temperature and 40° C.

Chemical Stability

The table below represents chemical stability of the compositions according to the invention at room temperature (RT) and 40° C. during 3 months.

| | | Compositions | | |
|---|---|---|---|---|
| Ivermectin titer (%/T0) | | 1 | 2 | 3 |
| 1 month | RT | NR | 99.5 (CV 0.2%) | 101.8 (CV 0.1%) |
| 2 months | RT | 97.2 (CV 0.4%) | 104 (CV 0.2%) | 102.9 (CV 0.6%) |
| | 40° C. | 99.4 (CV 0.3%) | 99.3 (CV 0.5%) | 98.8 (CV 0.6%) |
| 3 months | RT | 92.2 (CV 0.7%) | 100.1 (CV 0.5%) | 99.3 (CV 1.4%) |
| | 40° C. | 99.3 (CV 0.2%) | 100.1 (CV 0.9%) | 98.4 (CV 0.3%) |

NR: not reported
CV: coefficient of variation

Composition 1 is chemically stable two months at room temperature and chemically stable three months at 40° C.

Compositions 2 and 3 are chemically stable three months at room temperature and 40° C.

EXAMPLE 2

1) Preparation of the Compositions

The composition 4 according to the invention is formulated according to the following procedure:

In a first beaker, weigh the purified water and heat to 65° C. (±2° C.) then weigh the rest of the ingredients of the aqueous phase and mix all the aqueous phase.

In a second beaker, weigh the fatty phase without sorbitan monostearate, butylhydroxytoluene, dimethicone, propyl parahydroxybenzoate, heat at 65° C. (±2° C.), then weigh ivermectin and mix together. Then weigh sorbitan monostearate and butylhydroxytoluene and mix together. Weigh dimethicone and propyl parahydroxybenzoate then mix all the fatty phase.

Where the fatty and aqueous phases are at 65° C. (±2° C.), mix the two phases with Rayneri stirring at 900 rpm until complete homogeneity, and then cool.

Allow the emulsion to cool to 35° C. (±2° C.) then adjust the pH to 6.0 with the sodium hydroxide solution.

The composition 5 according to the invention is formulated according to the following procedure:

In a first beaker, weigh the carbomer polymer (Pemulen TR1) and the purified water, mix at 700 rpm and heat to 65° C. (±2° C.) then weigh the rest of the ingredients of the aqueous phase and mix all the aqueous phase.

In a second beaker, weigh the fatty phase without dimethicone, propyl parahydroxybenzoate and butylhydroxytoluene, heat at 65° C. (±2° C.), then weigh ivermectin and mix together. Then weigh butylhydroxytoluene and mix together. Weigh dimethicone and propyl parahydroxybenzoate then mix all the fatty phase.

Where the fatty and aqueous phases are at 65° C. (±2° C.), mix the two phases with Rayneri stirring at 900 rpm until complete homogeneity, and then cool.

Allow the emulsion to cool to 35° C. (±2° C.) then adjust the pH to 6.0 with the sodium hydroxide solution.

| | | 4 | 5 |
|---|---|---|---|
| | Ingredients | % by weight relative to the total weight of the composition | |
| Fatty phase | Ivermectin | 1 | 1 |
| | Isopropyl palmitate | 4 | 4 |
| | Cetyl alcohol | 3.5 | 3.5 |
| | Stearyl alcohol | 2.5 | 2.5 |
| | Ceteareth-20 | 3 | 3 |

-continued

| | Ingredients | 4 | 5 |
|---|---|---|---|
| | | % by weight relative to the total weight of the composition | |
| Aqueous phase | Sorbitan monostearate | 2 | — |
| | Dimethicone | 0.5 | 0.5 |
| | Propyl parahydroxybenzoate | 0.1 | 0.1 |
| | Butylhydroxytoluene | 0.1 | 0.1 |
| | Pemulen TR1 | — | 0.2 |
| | Glycerin | 4 | 4 |
| | Methyl parahydroxybenzoate | 0.2 | 0.2 |
| | Disodium EDTA | 0.05 | 0.05 |
| | Citric acid | 0.05 | 0.05 |
| | Purified water | qs 100 | qs 100 |
| | 10% sodium hydroxide | qs pH | qs pH |

2) Physical and Chemical Stability of the Compositions

Physical and Chemical Characteristics of the Compositions According to the Invention at T0 and at Room Temperature

| Composition | 4 | 5 |
|---|---|---|
| Macroscopic aspect | white cream | white cream |
| Microscopic aspect | liquid crystals from 3 µm to 15 µm | liquid crystals from 3 µm to 5 µm |
| pH | 6.20 | 6.16 |
| Viscosity (cP) | 3600 | 39040 |
| Ivermectin titer (%/label claim) | 97.1 (CV 0.0%) | 97.9 (CV 0.2%) |

CV: coefficient of variation

The viscosity is measured by the use of a Brookfield Viscometer (RV duII+Small sample adaptator Spindle 21 v=6 rpm for the composition 4; Small sample adaptator Spindle 34 v=6 rpm for the composition 5).

The compositions according to the invention are physically and chemically stable at T0 and at room temperature.

Physical Stability

The table below represents physical stability of the compositions according to the invention at 5° C., room temperature (RT) and 40° C. during two months.

| | 1 month | | | 2 months | | |
|---|---|---|---|---|---|---|
| Composition 4 | 5° C. | RT | 40° C. | 5° C. | RT | 40° C. |
| Macroscopic aspect | No change relative to T0 | | | No change relative to T0 | | |
| Microscopic aspect | No change relative to T0 | | | No change relative to T0 | | |
| pH | 6.22 | 6.15 | 6.10 | 6.13 | 6.13 | 6.14 |
| Viscosity (cP) | 4300 | 3800 | 4092 | 3792 | 3833 | 3808 |

| | 1 month | | | 2 months | | |
|---|---|---|---|---|---|---|
| Composition 5 | 5° C. | RT | 40° C. | 5° C. | RT | 40° C. |
| Macroscopic aspect | No change relative to T0 | | | No change relative to T0 | | |
| Microscopic aspect | No change relative to T0 | | | No change relative to T0 | | |
| pH | 6.37 | 6.38 | 6.34 | 6.39 | 6.37 | 6.44 |
| Viscosity (cP) | 43840 | 42880 | 42133 | 42880 | 41600 | 33173 |

Compositions 4 and 5 are physically stable two months at 5° C., room temperature and 40° C.

Chemical Stability

The table below represents chemical stability of the compositions according to the invention at room temperature (RT) and 40° C. during two months.

| | | Compositions | |
|---|---|---|---|
| Ivermectin titer (%/T0) | | 4 | 5 |
| 1 month | RT | 100.2 (CV 0.9%) | 100.1 (CV 0.2%) |
| | 40° C. | 99.8 (CV 0.5%) | 100.3 (CV 0.4%) |
| 2 months | RT | 100.2 (CV 0.0%) | 100.5 (CV 0.8%) |
| | 40° C. | 99.6 (CV 0.1%) | 100.2 (CV 0.1%) |

CV: coefficient of variation

Compositions 4 and 5 are chemically stable two months at room temperature and 40° C.

The invention claimed is:

1. A dermatological or pharmaceutical composition comprising:
   (a) at least one aqueous phase;
   (b) at least one fatty phase comprising (i) 5 to 10% by weight, relative to the total weight of the composition, of one or more fatty compounds selected from vegetable oils, mineral oils, animal oils, synthetic oils, silicone oils, fatty acids, fatty alcohols, fatty acid alcohol esters, waxes, gums, and mixtures thereof and (ii) at least one active compound chosen from avermectin compounds; and
   (c) 0.01 to 1% by weight, relative to the total weight of the composition, of one or more antioxidant agents chosen from the group consisting of butylhydroxyanisole, tocopherol, tocopherol acetate, ascorbic acid, ascorbic palmitate, propyl gallate, sodium metabisulfite, butylhydroxytoluene, and mixtures thereof,
   wherein the composition does not comprise solvents and/or propenetrating agents of avermectin compounds selected from the group consisting of propylene glycol, ethanol, isopropanol, butanol, N-methyl-2-pyrrolidone, dimethylsulfoxyde, polysorbate 80, poloxamer 124, phenoxyethanol, oleyl alcohol, isostearic acid, diisopropyl adipate, polypropylene glycol-15 stearyl ether ("PPG-15 stearyl ether"), octyl dodecanol, ethyl oleate, $C_{12}$-$C_{15}$ alkyl benzoate, and mixtures thereof.

2. The dermatological or pharmaceutical composition as defined in claim 1, wherein the avermectin compounds are chosen from ivermectin, invermectin, avermectin, abamectin, doramectin, eprinomectin and selamectin.

3. The dermatological or pharmaceutical composition as defined in claim 1, wherein the avermectin compound is ivermectin.

4. The dermatological or pharmaceutical composition as defined in claim 1, wherein the composition comprises from 0.01 to 10% by weight, of avermectin compounds, relative to the total weight of the composition.

5. The dermatological or pharmaceutical composition as defined in claim 4, wherein the composition comprises from 0.1 to 5% by weight of avermectin compounds, relative to the total weight of the composition.

6. The dermatological or pharmaceutical composition as defined in claim 1, wherein the fatty compounds are chosen from fatty acid alcohol esters, silicone oils, fatty alcohols, and mixtures thereof.

7. The dermatological or pharmaceutical composition as defined in claim 1, wherein the composition comprises one or more surfactants.

8. The dermatological or pharmaceutical composition as defined in claim 7, wherein the surfactants are chosen from non-ionic surfactants.

9. The dermatological or pharmaceutical composition as defined in claim 7, wherein the surfactants are chosen from polyoxyethylenated fatty alcohol ethers, sorbitan esters, and mixtures thereof.

10. The dermatological or pharmaceutical composition as defined in claim 7, wherein the composition comprises from 0.1 to 10% by weight of surfactants, relative to the total weight of the composition.

11. The dermatological or pharmaceutical composition as defined in claim 10, wherein the composition comprises from 1 to 7% by weight of surfactants, relative to the total weight of the composition.

12. The dermatological or pharmaceutical composition as defined in claim 1, wherein the composition comprises from 10 to 90% of fatty phase and from 10 to 90% of aqueous phase.

13. The dermatological or pharmaceutical composition as defined in claim 1, wherein the composition comprises from 10 to 30% of fatty phase and from 70 to 90% of aqueous phase.

14. A method of treating rosacea, of common acne, of seborrheic dermatitis, of perioral dermatitis, of acneiform rashes, of transient acantholytic dermatosis, of acne necrotica miliaris and of atopic dermatitis, comprising administering to a subject in need thereof a compositions as defined in claim 1.

15. The method as defined in claim 14, wherein the composition is administered topically.

* * * * *